(12) United States Patent
Dieckmann et al.

(10) Patent No.: US 8,097,562 B2
(45) Date of Patent: Jan. 17, 2012

(54) AGROCHEMICAL FORMULATIONS COMPRISING N-VINYLAMID CO-POLYMERS

(75) Inventors: Yvonne Dieckmann, Haßloch (DE); Michael Ishaque, Mannheim (DE); Ingo Münster, Böhl-leggelheim (DE); Laurent Picard, Bad Bergzabern (DE); Wolfgang Kerl, Mannheim (DE); Jürgen Langewald, Mannheim (DE); Klaus Kreuz, Denzlingen (DE); Harald Köhle, Bobenheim (DE); Felix Christian Görth, Sewickley, PA (US)

(73) Assignee: BASF SE, Ludwigshafen (DE)

( * ) Notice: Subject to any disclaimer, the term of this patent is extended or adjusted under 35 U.S.C. 154(b) by 414 days.

(21) Appl. No.: 12/516,683

(22) PCT Filed: Nov. 9, 2007

(86) PCT No.: PCT/EP2007/062118
§ 371 (c)(1),
(2), (4) Date: May 28, 2009

(87) PCT Pub. No.: WO2008/064987
PCT Pub. Date: Jun. 5, 2008

(65) Prior Publication Data
US 2010/0075850 A1     Mar. 25, 2010

(30) Foreign Application Priority Data
Nov. 30, 2006  (EP) .................... 06125065

(51) Int. Cl.
A01N 63/00 (2006.01)
A01N 35/00 (2006.01)
A01N 25/10 (2006.01)
C08L 83/00 (2006.01)
A61K 8/81 (2006.01)
C08F 26/00 (2006.01)
C08F 26/08 (2006.01)
C07C 53/00 (2006.01)
C07C 231/00 (2006.01)
C07C 233/00 (2006.01)
C07C 235/00 (2006.01)

(52) U.S. Cl. ........ 504/118; 504/326; 504/348; 504/360; 523/202; 524/808; 526/263; 526/264; 554/1; 554/51; 554/68; 554/69

(58) Field of Classification Search ............... 504/118, 504/326, 348, 360; 523/202; 524/808; 526/263, 526/264; 554/1, 51, 68, 69
See application file for complete search history.

(56) References Cited

U.S. PATENT DOCUMENTS

| | | | |
|---|---|---|---|
| 4,822,779 A | 4/1989 | Hwang et al. | |
| 5,169,951 A | 12/1992 | Sutter et al. | |
| 5,362,830 A | 11/1994 | Chuang et al. | |
| 5,948,917 A | 9/1999 | Adachi et al. | |
| 6,221,890 B1 | 4/2001 | Hatakoshi | |
| 6,335,357 B1 | 1/2002 | Okui et al. | |
| 2002/0028778 A1 | 3/2002 | Aven et al. | |
| 2003/0060471 A1 | 3/2003 | Okui et al. | |
| 2006/0167091 A1 | 7/2006 | Ishii et al. | |
| 2010/0048655 A1 | 2/2010 | Koltzenburg et al. | |
| 2010/0120617 A1 | 5/2010 | Dyllick-Brenzinger et al. | |
| 2010/0122379 A1 | 5/2010 | Dieckmann et al. | |

FOREIGN PATENT DOCUMENTS

| | | |
|---|---|---|
| EP | 454 621 | 10/1991 |
| EP | 462 456 | 12/1991 |
| JP | 2002-193709 | 7/2002 |
| JP | 2002/284608 | 10/2002 |
| JP | 2004-99597 | 4/2004 |

(Continued)

OTHER PUBLICATIONS

International Search Report for International Application No. PCT/EP2007/062118; International Filing Date: May 28, 2009; Date of Completion: Jan. 24, 2008; Date of Mailing: Feb. 5, 2008.
International Preliminary Report on Patentability for International Application No. PCT/EP2007/062118; International Filing Date: May 28, 2009; Date of Issuance: Jun. 3, 2009.
Odian, G., "Principles of polymerization", Wiley & Son, Inc., Publication, (2004) pp. 23-24, 4$^{th}$ ed.
Derwent Abstract 2003-233496-23 (for JP 2002284608).
Derwent Abstract 2002-638790/69 (for JP 2002193709).
Derwent Abstract 2003-229511/22 (for WO 03007717).
Derwent Abstract 2003-229512/22 (for WO 03007718).
Machine Translation for JP 2004-99597.

Primary Examiner — Johann Richter
Assistant Examiner — Jane C Oswecki
(74) Attorney, Agent, or Firm — Brinks Hofer Gilson & Lione

(57) ABSTRACT

The present invention comprises formulations comprising at least one pesticide and at least one co-polymer comprising (a) a N-vinylamid comonomer a) of formula (I) wherein $R^1$ and $R^2$ are independently of one another hydrogen or $C_1$-$C_4$ alkyl, preferably hydrogen or $R^1$ and $R^2$ represent together a —$(CH_2)_x$ moiety, which forms together with the nitrogen and the carbonyl-moiety a 5-8 membered ring, and (b) at least one comonomer b) selected from the group consisting of vinylpyrridin, vinylpyrridin derivatives and N-vinlyimidazole in polymerized form, methods of combating harmful insects and/or phytopathogenic fungi, a method of controlling undesired vegetation and methods of improving the health of plants based on the afore-mentioned formulations.

(I)

$$HC=CH_2$$
$$O=\overset{|}{\underset{R^2}{C}}-\overset{N-R^1}{}$$

14 Claims, No Drawings

FOREIGN PATENT DOCUMENTS

| | | |
|---|---|---|
| WO | WO 93/22380 | 11/1993 |
| WO | WO 98/28277 | 7/1998 |
| WO | WO 98/28279 | 7/1998 |
| WO | WO 9845274 | 10/1998 |
| WO | WO 01/00614 | 1/2001 |
| WO | WO 01/70671 | 7/2001 |
| WO | WO 02/48137 | 6/2002 |
| WO | WO 02/089579 | 11/2002 |
| WO | WO 02/090320 | 11/2002 |
| WO | WO 02/090321 | 11/2002 |
| WO | WO 03/007717 | 1/2003 |
| WO | WO 03/007718 | 1/2003 |
| WO | WO 03/015518 | 2/2003 |
| WO | WO 03/024222 | 3/2003 |
| WO | WO 2004/006677 | 1/2004 |
| WO | WO 2004/020399 | 3/2004 |
| WO | WO 2004/033468 | 4/2004 |
| WO | WO 2004/067528 | 8/2004 |
| WO | WO 2004/080180 | 9/2004 |
| WO | WO 2005/118552 | 12/2005 |
| WO | WO 2008/040786 | 4/2008 |
| WO | WO 2008/064986 | 6/2008 |
| WO | WO 2008/064990 | 6/2008 |
| WO | WO 2008/065050 | 6/2008 |
| WO | WO 2008/132067 | 11/2008 |
| WO | WO 2008/132179 | 11/2008 |

AGROCHEMICAL FORMULATIONS COMPRISING N-VINYLAMID CO-POLYMERS

This application is a National Stage application of International Application No. PCT/EP2007/062118 filed Nov. 9, 2007, the entire contents of which is hereby incorporated herein by reference. This application also claims the benefit under 35 U.S.C. §119 of European Patent Application No. 06125065.0, filed Nov. 30, 2006, the entire contents of which is hereby incorporated herein by reference.

The present invention comprises formulations comprising at least one pesticide and at least one co-polymer comprising
(a) a N-vinylamid comonomer a) of formula I

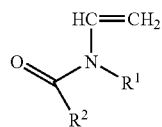

wherein $R^1$ and $R^2$ are independently of one another hydrogen or $C_1$-$C_4$ alkyl, preferably hydrogen or
$R^1$ and $R^2$ represent together a —$(CH_2)_x$— moiety, which forms together with the nitrogen and the carbonyl-moiety a 5-8 membered ring, and
(b) at least one comonomer b) selected from the group consisting of vinylpyrridin, vinylpyrridin derivatives and N-vinlyimidazole
in polymerized form, methods of combating harmful insects and/or phytopathogenic fungi, a method of controlling undesired vegetation and methods of improving the health of plants based on the afore-mentioned formulations.

Systemic pesticides provide the farmer lots of benefits: The uptake of pesticide of plants, which can be achieved either by seed treatment, foliar treatment or soil treatment, which is the simultaneous or sequential application of seeds and respective formulation (e.g. granule formulations), leads to plants, which are much longer resistant towards pests than plants treated with non-systemic pesticides.

Also for pesticides which provide plant health effects it is desirable to increase their uptake in the plant. The term "plant health" describes for example, advantageous properties such as improved crop characteristics including, but not limited to better emergence, increased crop yields, more favourable protein and/or content, more favourable aminoacid and/or oil composition, more developed root system (improved root growth), tillering increase, increase in plant height, bigger leaf blade, less dead basal leaves, stronger tillers, greener leaf colour, pigment content, photosynthetic activity, less fertilizers needed, less seeds needed, more productive tillers, earlier flowering, early grain maturity, less plant verse (lodging), increased shoot growth, enhanced plant vigor, increased plant stand or early germination; or a combination of at least two or more of the aforementioned effects or any other advantages familiar to a person skilled in the art.

Many pesticides, however, do not show satisfactory systemicity. Furthermore, the systemicity of already systemic pesticides leaves room for improvement.

It is therefore an object of the present invention to improve the systemicity of pesticides, preferably of pesticides with low or no systemicity.

Numerous polymers that are simply usefull as solubilizers are known in the art. However, whether any of these polymers is suitable for the above-mentioned purpose is not disclosed in prior art.

The object was solved by the provision of formulations comprising at least one pesticide and at least one co-polymer comprising
and at least one co-polymer comprising
(a) a N-vinylamid comonomer a) of formula I

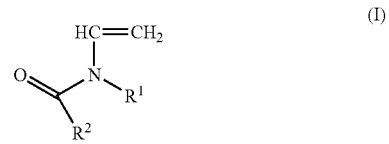

wherein $R^1$ and $R^2$ are independently of one another hydrogen or $C_1$-$C_4$ alkyl, preferably hydrogen or
$R^1$ and $R^2$ represent together a —$(CH_2)_x$— moiety, which forms together with the nitrogen and the carbonyl-moiety a 5-8 membered ring, preferably a 5 or 7 membered ring, most preferably a 5 membered ring; and
(b) at least one comonomer b) selected from the group consisting of vinylpyrridin, vinylpyrridin derivatives and N-vinlyimidazole
in polymerized form.

The term at least one at least one co-polymer means that one or more co-polymers as defined above can be present in the above-mentioned formulation, i.e. also mixtures of the above-defined co-polymers. Preferably, 1, 2 or 3, more preferably 1 or 2 most preferably 1 copolymer present in the above-mentioned formulation.

Comonomer a is present in the polymer with 90-10% by weight, preferably 75-25% by weight, most preferably 50% by weight.

Comonomer b is present in the polymer with 90-10% by weight, preferably 75-25% by weight, preferably 50% by weight.

Preferably, the % by weight data of the comonomer a) and b) of the copolymer add up to 100% by weight.

Preferred comonomers (a) are those, wherein $R^1$ and $R^2$ represent together a —$(CH_2)_x$— moiety, which forms together with the nitrogen and the carbonyl-moiety a 5-8 membered ring, preferably a 5 or 7 membered ring, most preferably a 5 membered ring, Preferred comonomers (b) are vinylpyrridin comonomers. Preferred vinylpyrridin comonomers 2-vinylpyridin, 3-vinylpyridin, 4-vinylpyridin or vinyl-2-methyl-5-pyridin, more preferably 2-vinlypyrridin, 3-vinlypyrridin or 4-vinlypyrridin, most preferably 2-vinlypyrridin or 4-vinlypyrridin, wherein 4 vinylpyrridin is utmost preferred.

The above-mentioned co-polymers may be block co-polymers, alternating co-polymers or statistic co-polymers, preferably statistic copolymers.

The pyridyl and imidazolyl moieties of comonomers (b) can be quaternized.

The conversion of comonomers (b) to quaternary compounds can take place during or, preferably, after the reaction. In the case of a subsequent conversion, the intermediate polymer can be isolated and purified first or converted directly. The conversion can be total or partial. Preferably at least 10%, particularly preferably at least 20% and very particularly preferably at least 30% of the incorporated comonomers (b) are converted to the corresponding quaternary form. The degree of conversion to quaternary compounds is preferably inversely proportional to the solubility of the comonomer (b) in water.

Preferably, the comonomers (b) are used for the polymerization in predominantly cationogenic form, i.e. more than 70, preferably more than 90, particularly preferably more than 95 and very particularly preferably more than 99 mol % cationogenic, i.e. not in quaternized or protonated form, and only converted to the cationic or protonated form by quaternization during or, particularly preferably, after the polymerization.

In one preferred embodiment of the invention the resulting co-polymer is partially or completely protonated or quaternized only during or, particularly preferably, after the polymerization, because the comonomer (b) used for the polymerization is preferably a comonomer that is only partially quaternized or protonated, if at all.

The comonomers (b) can either be used in protonated or quaternized form or, preferably, polymerized in unquaternized or unprotonated form, the copolymer obtained in the latter case being either quaternized or protonated during or, preferably, after the polymerization for the use according to the invention.

In the case where the comonomers are used in quaternized form, they can be used either as the dried substance, or in the form of concentrated solutions in solvents suitable for the comonomers, e.g. in polar solvents such as water, methanol, ethanol or acetone, or in the other co-monomer a) provided these are suitable as solvents.

The resulting co-polymers may also be protonated.

Examples of compounds suitable for the protonation are mineral acids such as HCl and $H_2SO_4$, monocarboxylic acids, e.g. formic acid and acetic acid, dicarboxylic acids and polyfunctional carboxylic acids, e.g. oxalic acid and citric acid, and any other protondonating compounds and substances that are capable of protonating the appropriate nitrogen atom. Water-soluble acids are particularly suitable for the protonation.

Possible organic acids which may be mentioned are optionally substituted monobasic and polybasic aliphatic and aromatic carboxylic acids, optionally substituted monobasic and polybasic aliphatic and aromatic sulfonic acids or optionally substituted monobasic and polybasic aliphatic and aromatic phosphonic acids.

Preferred organic acids are hydroxycarboxylic acids such as glycolic acid, lactic acid, tartaric acid and citric acid, lactic acid being particularly preferred.

Preferred inorganic acids which may be mentioned are phosphoric acid, phosphorous acid, sulfuric acid, sulfurous acid and hydrochloric acid, phosphoric acid being particularly preferred.

The polymer may be protonated either directly after the polymerization or only when the respective pesticide is formulated, during which the pH is normally adjusted to a physiologically acceptable value.

Protonation is understood as meaning that at least some of the protonatable groups of the polymer, preferably at least 20, preferably more than 50, particularly preferably more than 70 and very particularly preferably more than 90 mol %, are protonated, resulting in an overall cationic charge on the polymer.

Examples of suitable reagents for quaternizing the compounds a) are alkyl halides having 1 to 24 C atoms in the alkyl group, e.g. methyl chloride, methyl bromide, methyl iodide, ethyl chloride, ethyl bromide, propyl chloride, hexyl chloride, dodecyl chloride, lauryl chloride, propyl bromide, hexyl bromide, octyl bromide, decyl bromide, dodecyl bromide, and benzyl halides, especially benzyl chloride and benzyl bromide. Quaternization with long-chain alkyl radicals is preferably carried out with the corresponding alkyl bromides such as hexyl bromide, octylbromide, decylbromide, dodecyl bromide or lauryl bromide.

Other suitable quaternizing agents are dialkyl sulfates, especially dimethyl sulfate or diethyl sulfate.

The quaternization of the basic comonomers b) can also be carried out with alkylene oxides such as ethylene oxide or propylene oxide, in the presence of acids.

Preferred quaternizing agents are methyl chloride, dimethyl sulfate or diethyl sulfate, methyl chloride being particularly preferred.

The quaternization of the comonomers or polymers with one of said quaternizing agents can be effected by generally known methods.

The preparation is carried out by known processes, e.g. solution polymerization, precipitation polymerization or by inverse suspension polymerization using compounds which form free radicals under the polymerization conditions. The polymerisation can be carried out under reflux of the reaction mixture or under pressure.

The molar ratios of comonomer a):comonomer b) are 90:10 to 10:90, preferably 75:25 to 25:75, preferably 50:50.

The polymerization temperatures are usually in the range from 30 to 200° C., preferably 40 to 150° C.

Suitable azo compounds are 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl 2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), as free base or as hydrochloride, 2,2'-azobis(2-amidinopropane), as free base or as hydrochloride, 2,2'-azobis(2-methyl-N-[1,1-bis(hydroxymethyl)ethyl]propionamide) or 2,2'-azobis(2-methyl-N-[1,1-bis(hydroxymethyl)-2-hydroxyethyl]propionamide).

Suitable peroxides are, for example, acetylcyclohexanesulfonyl peroxide, diisopropyl peroxydicarbonate, t-amyl perneodecanoate, t-butyl perneodecanoate, t-butyl perpivalate, t-amyl perpivalate, bis(2,4-dichlorobenzoyl) peroxide, diisononanoyl peroxide, didecanoyl peroxide, dioctanoyl peroxide, dilauroyl peroxide, bis(2-methylbenzoyl) peroxide, disuccinoyl peroxide, diacetyl peroxide, dibenzoyl peroxide, t-butyl per-2-ethylhexanoate, bis(4-chlorobenzoyl) peroxide, t-butyl perisobutyrate, t-butyl permaleate, 1,1-bis(t-butylperoxy)-3,5,5-trimethylcyclohexane, 1,1-bis(t-butylperoxy)-cyclohexane, t-butylperoxy isopropyl carbonate, t-butyl perisononanoate, t-butyl peracetate, t-amyl perbenzoate, t-butyl perbenzoate, 2,2-bis(t-butylperoxy)butane, 2,2-bis-10-(t-butylperoxy)propane, dicumyl peroxide, 2,5-dimethyl-2,5-bis(t-butylperoxy)-hexane, 3-(t-butylperoxy)-3-phenylphthalide, di(t-amyl) peroxide, α,α'-bis(t-butylperoxyisopropyl)benzene, 3,5-bis(t-butylperoxy)-3,5-dimethyl-1,2-dioxolane, di(t-butyl) peroxide, 2,5-dimethyl-2,5-bis(t-butylperoxy)hexyne, 3,3,6,6,9,9-hexamethyl-1,2,4,5-tetraoxacyclononane, p-menthane hydroperoxide, pinane hydroperoxide, diisopropylbenzene, mono-α-hydroperoxide, cumene hydroperoxide or t-butyl hydroperoxide.

The reaction medium used is any customary solvent in which the comonomers are soluble. Preference is given to using water or alcoholic solvents, such as, for example, methanol, ethanol, n-propanol or isopropanol or mixtures of such alcohols with water.

In order to ensure that the reaction leads to homogeneous products, it is advantageous to supply the comonomers and the starter separately to the reaction solution. This can take place, for example, in the form of separate feeds for the individual reactants.

The polymerization can also be carried out in the presence of customary chain transfer agents if relatively low molecular weights are to be established.

The solids content of the organic solution obtained is usually 20 to 60% by weight, in particular 20 to 40% by weight.

A non-aqueous solvent used for the polymerization can then be removed by means of steam distillation and be replaced by water.

The aqueous solutions of the copolymers can, by various drying processes such as, for example, spray-drying, fluidized spray drying, drum drying or freeze-drying, be converted into powder form, from which an aqueous dispersion or solution can again be prepared by redispersion in water.

The copolymers used according to the invention can have weight average molecular weight values measured by gel permeation chromatography (G. Odian; Principles of Polymerization, 4$^{th}$ edition, Wiley & son 2004, pp. 23+24) from 20000-100000, preferably from 50000-100000 g/mol.

All embodiments of the above-mentioned polymers are referred herein below as "polymers according to the present invention".

The present invention also comprises the use of polymers according to the present invention for increasing the systemicity of pesticides. This is achieved contacting the pesticide with a certain amount of polymer according to the present invention e.g. in an agrochemical formulation as set forth above.

In general, the formulations comprise from 0.1 to 99% by weight of the polymer according to the present invention, preferably from 1 to 85% by weight, more preferably from 3 to 70% by weight, most preferably from 5 to 60% by weight.

In general, the formulations comprise from 0.1 to 90% by weight, preferably from 1 to 85% by weight, of the pesticide(s), more preferably from 3 to 80% by weight, most preferably from 3 to 70% by weight.

The weight by weight ratio of polymer:pesticide is preferably 20:1-1:20 (w/w), more preferably 10:1-1:10 (w/w), most preferably 3:1-1:3 (w/w).

The term "at least one pesticide" within the meaning of the invention states that one or more compounds can be selected from the group consisting of fungicides, insecticides, nematicides, herbicide and/or safener or growth regulator, preferably from the group consisting of fungicides, insecticides or nematicides, most preferably from the group consisting of fungicides. Also mixtures of pesticides of two or more the aforementioned classes can be used. The skilled artisan is familiar with such pesticides, which can be, for example, found in the Pesticide Manual, 13th Ed. (2003), The British Crop Protection Council, London.

The following list of pesticides is intended to illustrate the possible combinations, but not to impose any limitation:

The insecticide/nematicide is selected from the group consisting of

The following list of pesticides together with which the compounds according to the invention can be used, is intended to illustrate the possible combinations, but not to impose any limitation:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

A.5. Nicotinic receptor agonists/antagonists compounds: clothianidin, dinotefuran, imidacloprid, thiamethoxam, nitenpyram, acetamiprid, thiacloprid; the thiazol compound of formula ($\Delta^1$)

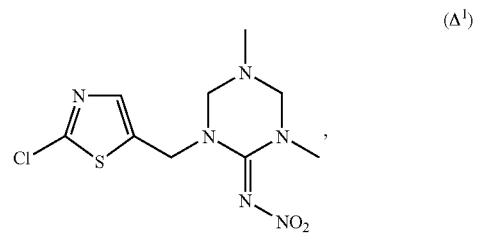

A.6. GABA antagonist compounds: acetoprole, endosulfan, ethiprole, fipronil, vaniliprole, pyrafluprole, pyriprole, the phenylpyrazole compound of formula $\Delta^2$

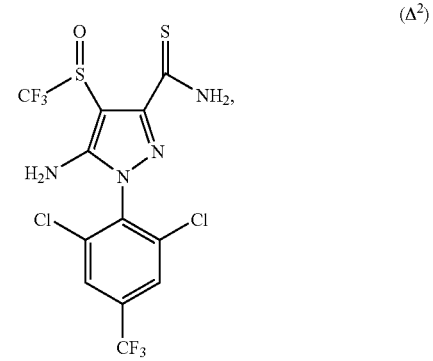

A.7. Macrocyclic lactone insecticides: abamectin, emamectin, milbemectin, lepimectin, spinosad, the compound of formula ($\Delta^3$) (CAS No. 187166-40-1)

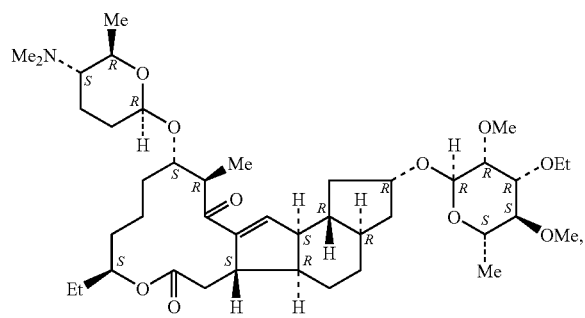

(A³)

A.8. METI I compounds: fenazaquin, pyridaben, tebufenpyrad, tolfenpyrad, flufenerim;
A.9. METI II and III compounds: acequinocyl, fluacyprim, hydramethylnon;
A.10. Uncoupler compounds: chlorfenapyr;
A.11. Oxidative phosphorylation inhibitor compounds: cyhexatin, diafenthiuron, fenbutatin oxide, propargite;
A.12. Moulting disruptor compounds: cyromazine;
A.13. Mixed Function Oxidase inhibitor compounds: piperonyl butoxide;
A.14. Sodium channel blocker compounds: indoxacarb, metaflumizone,
A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula $\Delta^4$

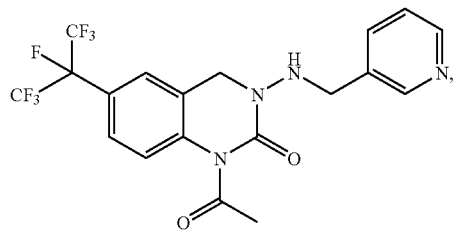

(A⁴)

N—R'-2,2-dihalo-1-R''cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R'' is hydrogen or methyl and R''' is methyl or ethyl, anthranilamide compounds of formula $\Delta^5$

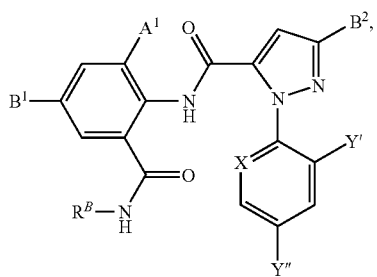

(A⁵)

wherein $A^1$ is $CH_3$, Cl, Br, I, X is C—H, C—Cl, C—F or N, Y' is F, Cl, or Br, Y'' is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and malononitrile compounds as described in JP 2002 284608, WO 02/89579, WO 02/90320, WO 02/90321, WO 04/06677, WO 04/20399, or JP 2004 99597.

The commercially available compounds of the group A may be found in The Pesticide Manual, 13th Edition, British Crop Protection Council (2003) among other publications. Thiamides of formula $\Delta^2$ and their preparation have been described in WO 98/28279. Lepimection is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180.

Anthranilamides of formula $\Delta^5$ and their preparation have been described in WO 01/70671; WO 02/48137; WO 03/24222, WO 03/15518, WO 04/67528; WO 04/33468; and WO 05/118552.

The fungicide can be selected from the group consisting of
1. Strobilurins such as azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho-((2,5-dimethylphenyloxymethylene)phenyl)-3-methoxyacrylate;
2. Carboxamides such as
carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide; carboxylic acid morpholides: dimethomorph, flumorph;
benzamides: flumetover, fluopicolide (picobenzamid), zoxamide;
other carboxamides: carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide; N-(3',4'-dichloro-5-fluorobiphenyl-2-yl)-3-difluoromethyl-1-methylpyrazole-4-carboxamide and 3-Difluoromethyl-1-methyl-1H-pyrazole-4-carboxylic acid (2-bicyclopropyl-2-yl-phenyl)-amide;
3. Azoles such as
triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;
  imidazoles: cyazofamid, imazalil, pefurazoate, prochloraz, triflumizole;
  benzimidazoles: benomyl, carbendazim, fuberidazole, thiabendazole;
  others: ethaboxam, etridiazole, hymexazole;
4. Nitrogenous heterocyclyl compounds such as
  pyridines: fluazinam, pyrifenox, 3-[5-(4-chlorophenyl)-2,3-dimethylisoxazolidin-3-yl]-pyridine;
  pyrimidines: bupirimate, cyprodinil, ferimzone, fenarimol, mepanipyrim, nuarimol, pyrimethanil;
  piperazines: triforine;
  pyrroles: fludioxonil, fenpiclonil;
  morpholines: aldimorph, dodemorph, fenpropimorph, tridemorph;
  dicarboximides: iprodione, procymidone, vinclozolin;
  others: acibenzolar-S-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;
5. Carbamates and dithiocarbamates such as
  dithiocarbamates: ferbam, mancozeb, maneb, metiram, metam, propineb, thiram, zineb, ziram;
  carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate;
6. Other fungicides such as
  guanidines: dodine, iminoctadine, guazatine;
  antibiotics: kasugamycin, polyoxins, streptomycin, validamycin A;
  organometallic compounds: fentin salts;
  sulfur-containing heterocyclyl compounds: isoprothiolane, dithianon;
  organophosphorus compounds: edifenphos, fosetyl, fosetyl-aluminum, iprobenfos, pyrazophos, tolclofos-methyl, phosphorous acid and its salts;
  organochlorine compounds: thiophanate-methyl, chlorothalonil, dichlofluanid, tolylfluanid, flusulfamide, phthalide, hexachlorbenzene, pencycuron, quintozene;
  nitrophenyl derivatives: binapacryl, dinocap, dinobuton;
  inorganic active compounds: Bordeaux mixture, copper acetate, copper hydroxide, copper oxychloride, basic copper sulfate, sulfur;
  others: spiroxamine, cyflufenamid, cymoxanil, metrafenone The herbicide is selected from the group consisting of
b1) lipid biosynthesis inhibitors such as chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;

b2) ALS inhibitors such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

b3) photosynthesis inhibitors such as atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

b4) protoporphyrinogen-IX oxidase inhibitors such as acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

b5) bleacher herbicides such as metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl) pyrimidine, and also 3-heterocyclyl-substituted benzoyl derivatives of the formula II (see in WO 96/26202, WO 97/41116, WO 97/41117 and WO 97/41118)

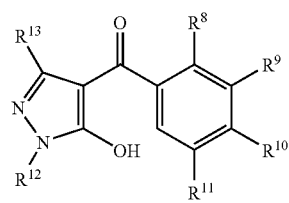

in which the variables $R^8$ to $R^{13}$ are as defined below:

$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;

$R^9$ is a heterocyclic radical selected from the group consisting of such as thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted, e.g. mono-, di-, tri- or tetrasubstituted, by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;

$R^{12}$ is $C_1$-$C_6$-alkyl;

$R^{13}$ is hydrogen or $C_1$-$C_6$-alkyl.

b6) EPSP synthase inhibitors such as glyphosate;

b7) glutamine synthase inhibitors such as glufosinate and bilanaphos;

b8) DHP synthase inhibitors such as asulam;

b9) mitose inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

b10) VLCFA inhibitors such as acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) cellulose biosynthesis inhibitors such as dichlobenil, chlorthiamid, isoxaben and flupoxam;

b12) decoupler herbicides such as dinofenate, dinoprop, dinosam, dinoseb, dinoterb, DNOC, etinofen and medinoterb;

b13) auxin herbicides such as clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazolin;

b14) auxin transport inhibitors such as naptalam, diflufenzopyr;

b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

Suitable safeners can be selected from the following listing: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine (R-29148), 4-(dichloroacetyl)-1-oxa-4-azaspiro[4.5]decane (AD-67; MON 4660) and oxabetrinil Generally, fungicides and insecticides are preferred.

Preferred insecticides are azinphos-methyl, chlorpyrifos, chlorpyrifos-methyl, chlorfenvinphos, diazinon, disulfoton, ethion, fenitrothion, fenthion, isoxathion, malathion, methidathion, methyl-parathion, parathion, phenthoate, phosalone, phosmet, phorate, phoxim, pirimiphos-methyl, profenofos, prothiofos, sulprofos, tetrachlorvinphos, terbufos, alanycarb, benfuracarb, carbosulfan, fenoxycarb, furathiocarb, methiocarb, triazamate; chlorfluazuron, diflubenzuron, flucycloxuron, flufenoxuron, hexaflumuron, lufenuron, novaluron, teflubenzuron, triflumuron; methoxyfenozide, tebufenozide, azadirachtin pyriproxyfen, methoprene, fenoxycarb; spirodiclofen, spiromesifen, spirotetramat; clothianidin, dinotefuran, imidacloprid, thiamethoxam, nitenpyram, acetamiprid, thiacloprid; acetoprole, endosulfan, ethiprole, fipronil, vaniliprole, pyrafluprole, pyriprole, the phenylpyrazole compound of formula $\Delta^2$

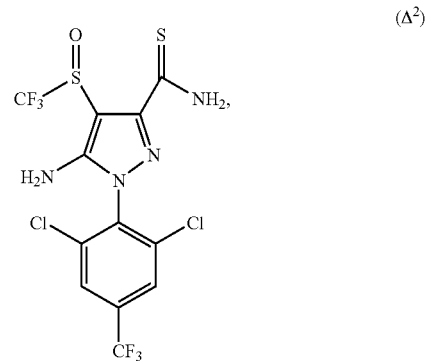

($\Delta^2$)

abamectin, emamectin, milbemectin, lepimectin, fenazaquin, pyridaben, tebufenpyrad, acequinocyl, fluacyprim, hydramethylnon, chlorfenapyr, cyhexatin, diafenthiuron, fenbutatin oxide, propargite; piperonyl butoxide; indoxacarb, metaflumizone, bifenazate, pymetrozine, N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl More preferred insecticides are cyfluthrin, λ-cyhalothrin, cypermethrin, alpha-cypermethrin, beta-cypermethrin, deltamethrin, esfenvalerate, fenvalerate, permethrin, tefluthrin, tetramethrin, transfluthrin, flufenoxuron, teflubenzuron, clothianidin, thiamethoxam, acetamiprid, ethiprole, fipronil, phenylpyrazole compound of formula $\Delta^2$

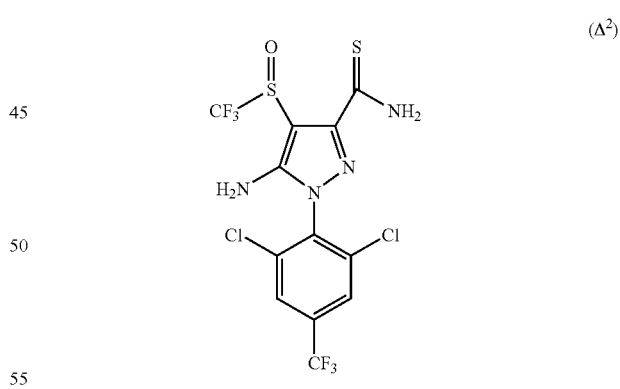

($\Delta^2$)

chlorfenapyr; piperonyl butoxide; indoxacarb, metaflumizone, pymetrozine, N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl.

Preferred fungicides are azoxystrobin, dimoxystrobin, fluoxastrobin, kresoxim-methyl, picoxystrobin, pyraclostrobin, trifloxystrobin, orysastrobin, methyl 2-(ortho-((2,5-dimethylphenyloxymethylene)phenyl)-3-methoxyacrylate; boscalid, metalaxyl, penthiopyrad, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid, N-(3',4'-dichloro-5-fluorobiphenyl-2-yl)-3-difluoromethyl-1-methylpyrazole-4-carboxamide, 3-Difluoromethyl-1-methyl-1H-pyrazole-4-carboxylic acid (2-bicyclopropyl-2-yl-phenyl)-amide, cyproconazole, difenoconazole, epoxiconazole, fluquinconazole, metconazole, propiconazole, prothioconazole, tebuconazole, triticonazole; cyazofamid, prochloraz, ethaboxam, fluazinam, cyprodinil, pyrimethanil; triforine; fludioxonil, dodemorph, fenpropimorph, tridemorph, vinclozolin, dazomet, fenoxanil, fenpropidin, proquinazid; flubenthiavalicarb, iprovalicarb, dodine, dithianon, fosetyl, fosetyl-aluminum, chlorothalonil, spiroxamine, cyflufenamid, cymoxanil, metrafenone.

More preferred fungicides are azoxystrobin, dimoxystrobin, fluoxastrobin, kresoxim-methyl, picoxystrobin, pyraclostrobin, trifloxystrobin, orysastrobin, boscalid, metalaxyl, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid, N-(3', 4'-dichloro-5-fluorobiphenyl-2-yl)-3-difluoromethyl-1-methylpyrazole-4-carboxamide, 3-Difluoromethyl-1-methyl-1H-pyrazole-4-carboxylic acid (2-bicyclopropyl-2-yl-phenyl)-amide, cyproconazole, difenoconazole, epoxiconazole, metconazole, propiconazole, prothioconazole, tebuconazole, cyazofamid, prochloraz, cyprodinil, triforine; fludioxonil, dodemorph, fenpropimorph, tridemorph, vinclozolin, dazomet, fenoxanil, iprovalicarb, dodine, dithianon, fosetyl, fosetyl-aluminum, chlorothalonil, spiroxamine, metrafenone.

Most preferred fungicides are azoxystrobin, fluoxastrobin, picoxystrobin, pyraclostrobin, trifloxystrobin, orysastrobin, boscalid, metalaxyl, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid, 3-Difluoromethyl-1-methyl-1H-pyrazole-4-carboxylic acid (2-bicyclopropyl-2-yl-phenyl)-amide, cyproconazole, difenoconazole, epoxiconazole, propiconazole, prothioconazole, tebuconazole, prochloraz, cyprodinil, fludioxonil, iprovalicarb, fosetyl, fosetyl-aluminum, chlorothalonil, spiroxamine, metrafenone.

As mentioned above, in one embodiment of the invention, also pesticides can be used, which confer plant health effects. Such pesticides are known in the art. Suitable for this purpose are, for example an active compound that inhibits the mitochondrial breathing chain at the level of the b/c1 complex;

carboxylic amides selected from benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamid, tiadinil, 4-difluoromethyl-2-methyl-thiazol-5-carboxylic acid-(4'-bromo-biphenyl-2-yl)-amide, 4-difluoromethyl-2-methyl-thiazol-5-carboxylic acid-(4'-trifluoromethyl-biphenyl-2-yl)-amide, 4-difluoromethyl-2-methyl-thiazol-5-carboxylic acid-(4'-chloro-3'-fluoro-biphenyl-2-yl)-amide, 3-difluoromethyl-1-methyl-pyrazol-4-carboxylic acid-(3',4'-dichloro-4-fluoro-biphenyl-2-yl)-amide, 3,4-dichloro-isothiazol-5-carboxylic acid-(2-cyano-phenyl)-amide, dimethomorph, flumorph, flumetover, fluopicolide (picobenzamid), zoxamide, carpropamide, diclocymet, mandipropamid, N-(2-(4-[3-(4-chloro-phenyl)-prop-2-inyloxy]-3-methoxy-phenyl)-ethyl)-2-methanesulfonylamino-3-methyl-butyramid and N-(2-(4-[3-(4-chloro-phenyl)-prop-2-inyloxy]-3-methoxy-phenyl)-ethyl)-2-ethanesulfonylamino-3-methyl-butyramide;

azoles selected from bitertanole, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, cyazofamid, imazalil, pefurazoate, prochloraz, triflumizol, benomyl, carbendazim, fuberidazole, thiabendazole, ethaboxam, etridiazole and hymexazole;

nitrogen-containing heterocyclic compounds selected from fluazinam, pyrifenox, 3-[5-(4-chloro-phenyl)-2,3-dimethyl-isoxazolidin-3-yl]-pyridine, bupirimat, cyprodinil, ferimzon, fenarimol, mepanipyrim, nuarimol, pyrimethanil, triforin, fludioxonil, fenpiclonil, aldimorph, dodemorph, fenpropimorph, tridemorph, iprodion, procymidon, vinclozolin, acibenzolar-S-methyl, anilazin, captan, captafol, dazomet, diclomezine, fenoxanil, folpet, fenpropidin, famoxadone, fenamidone, octhilinon, probenazol, proquinazid, pyroquilon, quinoxyfen, tricyclazol, 2-butoxy-6-iodo-3-propyl-chromen-4-one, 3-(3-bromo-6-fluoro-2-methyl-indole-1-sulfonyl)-[1,2,4]triazole-1-sulfonic acid dimethylamide; carbamates and dithiocarbamates selected from ferbam, mancozeb, metiram, metam, propineb, thiram, zineb, ziram, diethofencarb, flubenthiavalicarb, iprovalicarb, propamocarb, 3-(4-chloro-phenyl)-3-(2-isopropoxycarbonylamino-3-methyl-butyrylamino)-propionic acid methylester and N-(1-(1-(4-cyanophenyl)ethanesulfonyl)-but-2-yl) carbamic acid-(4-fluorophenyl)ester;

guanidines selected from dodin, iminoctadine and guazatin; antibiotics selected from kasugamycin, polyoxine, streptomycin and validamycin A; fentin salts;

sulfur-containing heterocyclic compounds selected from isoprothiolan and dithianon; organophosphorous compounds selected from edifenphos, fosetyl, fosetyl-aluminium, iprobenfos, pyrazophos, tolclofos-methyl, phosphoric acid and the salts thereof; organo-chloro compounds selected from thiophanate methyl, chlorothalonil, dichlofluanid, tolylfluanid, flusulfamid, phthalide, hexachlorbenzene, pencycuron, quintozen; nitrophenyl derivatives selected from binapacryl, dinocap and dinobuton;

inorganic active ingredients selected from Bordeaux composition, copper acetate, copper hydroxide, copper oxychloride, basic copper sulfate and sulfur;

spiroxamine; cyflufenamide; cymoxanil; metrafenone;

organo(thio)phosphates selected from acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos and trichlorfon;

carbamates selected from alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicar and triazamate;

pyrethroids selected from allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin and profluthrin, dimefluthrin;

growth regulators selected from a) chitin synthesis inhibitors that are selected from the benzoylureas chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole and clofentazine; b) ecdysone antagonists that are selected from halofenozide, methoxyfenozide, tebufenozide and azadirachtin; c) juvenoids that are selected from pyriproxyfen, methoprene and fenoxycarb and d) lipid biosynthesis inhibitors that are selected from spirodiclofen, spiromesifen and spirotetramat; nicotinic receptor agonists/antagonists compounds selected from clothianidin, dinotefuran, (EZ)-1-(6-chloro-3-pyridyl-methyl)-N-nitroimidazolidin-2-ylideneamine (imidacloprid), (EZ)-3-(2-chloro-1,3-thiazol-5-ylmethyl)-5-methyl-1,3,5-oxadiazinan-4-ylidene(nitro)amine (thiamethoxam), nitenpyram, acetamiprid, thiacloprid; the thiazol compound of formula ($\Gamma^1$)

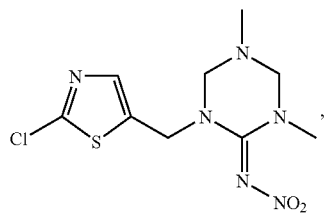

GABA antagonist compounds selected from acetoprole, endosulfan, ethiprole, 5-amino-1-(2,6-dichloro-α,α,α-trifluoro-p-tolyl)-4-trifluoromethylsulfinylpyrazole-3-carbonitrile (fipronil), vaniliprole, pyrafluprole, pyriprole and the phenylpyrazole compound of formula $\Gamma^2$

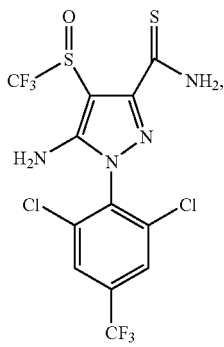

METI I compounds selected from fenazaquin, pyridaben, tebufenpyrad, tolfenpyrad and flufenerim;

METI II and III compounds selected from acequinocyl, fluacyprim and hydramethylnon; chlorfenapyr;

oxidative phosphorylation inhibitor compounds selected from cyhexatin, diafenthiuron, fenbutatin oxide and propargite;

cyromazine; piperonyl butoxide; indoxacarb; benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula $\Gamma^4$

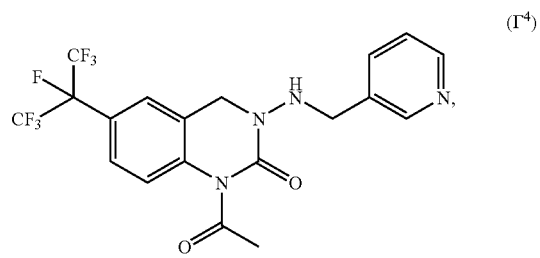

and anthranilamide compounds of formula $\Gamma^5$

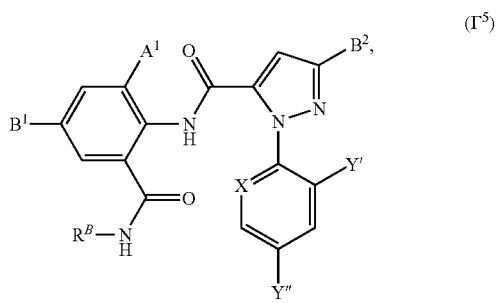

wherein $A^1$ is $CH_3$, Cl, Br, I, X is C—H, C—Cl, C—F or N, Y' is F, Cl, or Br, Y" is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$.

wherein pyraclostrobin, azoxystrobin, kresoximmethyl, trifloxystrobin, picoxystrobin, dimoxystrobin, fluoxastrobin, orysastrobin, tebuconazole, difenoconazole, epoxiconazole, cyproconazole, prothioconazol, propiconazole, fipronil, imidacloprid and thiamethoxam are preferred.

As set forth above, the polymers according to the present invention can be used for the preparation of formulations comprising at least one pesticide and the polymer according to the present invention. Optionally, formulations comprising at least one pesticide and at least one polymer according to the present invention may comprise further formulation auxiliaries.

In general, the formulations comprise from 0 to 90% by weight, preferably from 1 to 85% by weight, more preferably from 5 to 80% by weight, most preferably from 5 to 65% by weight of the formulation auxiliaries.

The term "formulation auxiliaries" within the meaning of the invention is auxiliaries suitable for the formulation of pesticides, such as further solvents and/or carriers and/or surfactants (ionic or non-ionic surfactants, adjuvants, dispersing agents) and/or preservatives and/or antifoaming agents and/or anti-freezing agents and optionally, for seed treatment formulations colorants and/or binders and/or gelling agents and/or thickeners.

Examples of suitable solvents are water, aromatic solvents (for example Solvesso products, xylene), paraffins (for example mineral oil fractions such as kerosene or diesel oil), coal tar oils and oils of vegetable or animal origin, aliphatic, cyclic and aromatic hydrocarbons, for example toluene, xylene, paraffin, tetrahydronaphthalene, alkylated naphthalenes or their derivatives, alcohols (for example methanol, butanol, pentanol, benzyl alcohol, cyclohexanol), ketones (for example cyclohexanone, gamma-butyrolactone), pyrrolidones (NMP, NEP, NOP), acetates (glycol diacetate), glycols, fatty acid dimethylamides, fatty acids and fatty acid esters, isophorone and dimethylsulfoxide. In principle, solvent mixtures may also be used.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, tristearylphenyl polyglycol ethers, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Examples of suitable carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders, polyvinylpyrrolidone and other solid carriers.).

Also anti-freezing agents such as glycerin, ethylene glycol, hexylene glycol, propylene glycol and bactericides such as can be added to the formulation.

Suitable antifoaming agents are for example antifoaming agents based on silicon or magnesium stearate.

Suitable preservatives are for example 1,2-benzisothiazolin-3-one and/or 2-Methyl-2H-isothiazol-3-one or sodium benzoate or benzoic acid.

Examples of thickeners (i.e., compounds which bestow a pseudoplastic flow behavior on the formulation, i.e. high viscosity at rest and low viscosity in the agitated state) are, for example, polysaccharides or organic or inorganic layered minerals, such as xanthan gum (Kelzan® from Kelco), Rhodopol® 23 (Rhône-Poulenc) or Veegum® (R.T. Vanderbilt) or Attaclay® (Engelhardt).

Seed Treatment formulations may additionally comprise binders and optionally colorants.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Binders can be added to improve the adhesion of the active materials on the seeds after treatment. Suitable binders are: polyvinylpyrrolidone, polyvinylacetate, polyvinylalkohol and tylose.

The use forms of the formulations (for example in the form of directly sprayable solutions, powders, suspensions or dispersions, emulsions, oil dispersions, pastes, dustable products, materials for spreading, or granules) depend entirely on the intended purposes; they are intended to ensure in each case the finest possible distribution of the pesticide and polymer according to the invention.

Examples of suitable formulation types in which the polymer according to the present invention can be used are
1. Liquid Formulations such as
EC (Emulsifiable concentrate) formulation; SL or LS (Soluble concentrate) formulation; EW (Emulsion, oil in water) formulation ME (Microemulsion) formulation MEC Microemulsifiable concentrates concentrate formulation CS (Capsule suspension) formulation TK (Technical concentrate) formulation, OD (oil based suspension concentrate) formulation; SC (suspension concentrate) formulation; SE (Suspo-emulsion) formulation; ULV (Ultra-low volume liquid) formulation; SO (Spreading oil) formulation; AL (Any other liquid) formulation; LA (Lacquer) formulation; DC (Dispersible concentrate) formulation;
2. Solid Formulations such as
WG (Water dispersible granules) formulation; TB (Tablet) formulation; FG (Fine granule) formulation; MG (Microgranule) formulation; SG (soluble Granule)

Preferred are formulation types such as EC (Emulsifiable concentrate) formulation; SL or LS (Soluble concentrate) formulation; EW (Emulsion, oil in water) formulation ME (Microemulsion) formulation, CS (Capsule suspension) formulation, OD (oil based suspension concentrate) formulation; SC (suspension concentrate) formulation; SE (Suspoemulsion) formulation; DC (Dispersible concentrate) formulation, WG (Water dispersible granules) formulation; TB (Tablet) formulation); FG (Fine granule) formulation and SG (soluble Granule).

The invention also includes a process for the preparation of a formulation according to the present invention. The processes used in this connection are generally familiar to a person skilled in the art and are, for example, described in the literature cited with the various formulation types (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8).

Liquid formulations can be prepared by mixing or combining the polymer according to the invention with at least one pesticide and or further formulation auxiliaries.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

The above-referred formulations can be used as such or use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the pesticid(es) and polymer according to the invention.

Aqueous use forms can be prepared also from emulsion concentrates, pastes or wettable powders (sprayable powders, oil dispersions) by adding a suitable solvent, for example water.

In general, the polymer according to the present invention can be added to an already prepared formulation or included in a formulation comprising at least one pesticide and at least one polymer according to the present invention. The addition of the polymer to the formulation can be performed prior or after dilution of the formulation in water; e.g. preparing a formulation as mentioned before containing the polymer according to this invention or adding the polymer after dilution of the pesticide formulation in a suitable solvent, for example water (e.g. as so called tank mix)

All embodiments of the above-mentioned application are herein below referred to as "formulation according to the present invention".

The present invention furthermore comprises a method of combating harmful insects and/or phytopathogenic fungi, which comprises contacting plants, seed, soil or habitat of plants in or on which the harmful insects and/or phytopathogenic fungi are growing or may grow, plants, seed or soil to be protected from attack or infestation by said harmful insects and/or phytopathogenic fungi with an effective amount of a agrochemical formulation according to the present invention.

The formulations according to the present invention can therefore be used for the control of a multitude of phytopaghogenic fungi or insects on various cultivated plants or weeds in, such as wheat, rye, barley, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants.

The present invention furthermore comprises a method of improving the health of plants, which comprises applying a formulation according to the present invention, wherein the pesticide is a pesticide which confers plant health effects, to plants, parts of plants, or the locus where plants grow.

The present invention furthermore comprises a method of controlling undesired vegetation, which comprises allowing a herbicidally effective amount of a agrochemical formulation according to the present invention to act on plants, their habitat or on seed of said plants.

Thus, the formulations according to the present invention compositions according to the present invention are suitable for controlling common harmful plants in useful plants, in particular in crops such as oat, barley, millet, corn, rice, wheat, sugar cane, cotton, oilseed rape, flax, lentil, sugar beet, tobacco, sunflowers and soybeans or in perennial crops.

The term phytopathogenic fungi includes but is not limited to the following species:

*Alternaria* species on vegetables, rapeseed, sugar beet and fruit and rice (for example *A. solani* or *A. alternate* on potato and other plants); *Aphanomyces* species on sugar beet and vegetables; *Bipolaris* and *Drechslera* species on corn, cereals, rice and lawns (for example *D. teres* on barley, *D. tritci-repentis* on wheat); *Blumeria graminis* (powdery mildew) on cereals; *Botrytis cinerea* (gray mold) on strawberries, vegetables, flowers and grapevines; *Bremia lactucae* on lettuce; *Cercospora* species on corn, soybeans, rice and sugar beet (for example *C. beticula* on sugar beet); *Cochliobolus* species on corn, cereals, rice (for example *Cochliobolus sativus* on cereals, *Cochliobolus miyabeanus* on rice); *Colletotricum* species on soybeans, cotton and other plants (for example *C. acutatum* on various plants); Esca on grapes caused by *Phaeoacremonium chlamydosporium, Ph. Aleophilum,* and *Formitipora punctata* (syn. *Phellinus punctatus*); *Exserohilum* species on corn; *Erysiphe cichoracearum* and *Sphaerothecai fuliginea* on cucurbits; *Fusarium* and *Verticillium* species (for example *V. dahliae*) on various plants (for example *F. graminearum* on wheat); *Gaeumanomyces graminis* on cereals; *Gibberella* species on cereals and rice (for example *Gibberella fujikuroi* on rice); Grainstaining complex on rice; *Helminthosporium* species (for example *H. graminicola*) on corn and rice; *Michrodochium nivale* on cereals; *Mycosphaerella* species on cereals, bananas and peanuts (*M. graminicola* on wheat, *M. fijiesis* on bananas); *Phakopsara pachyrhizi* and *Phakopsara meibomiae* on soybeans; *Phomopsis* species on soybeans, sunflowers and grapevines (*P. viticola* on grapevines, *P. helianthii* on sunflowers); *Phytophthora infestans* on potatoes and tomatoes; *Plasmopara viticola* on grapevines; *Podosphaera leucotricha* on apples; *Pseudocercosporella herpotrichoides* on cereals; *Pseudoperonospora* species on hops and cucurbits (for example *P. cubenis* on cucumbers); *Puccinia* species on cereals, corn and asparagus (*P. triticina* and *P. striformis* on wheat, *P. asparagi* on asparagus); *Pyrenophora* species on cereals; *Pyricularia oryzae, Corticium sasakii, Sarocladium oryzae, S. attenuatum, Entyloma oryzae* on rice; *Pyricularia grisea* on lawns and cereals; *Pythium* spp. on lawns, rice, corn, cotton, rapeseed, sunflowers, sugar beet, vegetables and other plants; *Rhizoctonia*-species (for example *R. solani*) on cotton, rice, potatoes, lawns, corn, rapeseed, potatoes, sugar beet, vegetables and other plants; *Rhynchosporium secalis* e.g. on rye and barley; *Sclerotinia* species (for example *S. sclerotiorum*) on rapeseed, sunflowers and other plants; *Septoria tritici* and *Stagonospora nodorum* on wheat; *Erysiphe* (syn. *Uncinula necator*) on grapevines; *Setospaeria* species on corn and lawns; *Sphace-lotheca reilinia* on corn; *Thievaliopsis* species on soybeans and cotton; *Tilletia* species on cereals; *Ustilago* species on cereals, corn and sugar beet and; *Venturia* species (scab) on apples and pears (for example *V. inaequalis* on apples). They are particularly suitable for controlling harmful fungi from the class of the Oomycetes, such as *Peronospora* species, *Phytophthora* species, *Plasmopara viticola* and *Pseudoperonospora* species.

The formulations according to the present invention can also be used for controlling harmful fungi in the protection of material such as wood. Examples of fungi are Ascomycetes, such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp.

The invention furthermore relates to a method for controlling undesirable vegetation in crops, in particular in crops of oat, barley, millet, corn, rice, wheat, sugar cane, cotton, oilseed rape, flax, lentil, sugar beet, tobacco, sunflowers and soybeans or in perennial crops, which comprises allowing a effective amount of a agrochemical formulation according to the present invention to act on plants, their habitat or on seed of said plants.

The invention furthermore relates to a method for controlling undesirable vegetation in crops which, by genetic engineering or by breeding, are resistant to one or more herbicides and/or fungicides and/or or to attack by insects, which comprises allowing a effective amount of a agrochemical formulation according to the present invention to act on plants, their habitat or on seed of said plants.

The control of undesired vegetation is understood as meaning the destruction of weeds. Weeds, in the broadest sense, are understood as meaning all those plants which grow in locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.*

Thus, as set forth above, formulations according to the invention can be applied via various methods.

In one embodiment of the present invention, foliar application of the formulation according to the present invention is carried out, e.g. by spraying or dusting or otherwise applying the mixture to the seeds, the seedlings, the plants.

Another embodiment of the present invention comprises soil treatment, e.g by spraying or dusting or otherwise applying the mixture to the soils before (e.g. by soil drench) or after sowing of the plants or before or after emergence of the plants.

In accordance with one variant of soil application, a further subject of the invention is a method of treating soil by the application, in particular into the seed drill In accordance with one variant of soil application, a further subject of the invention is in furrow treatment, which comprises adding a solid or liquid formulation to the open furrow, in which seeds have been sown or, alternatively, applying seeds and formulation simultaneously to the open furrow Another embodiment of the present invention comprises the treatment of seeds or seedlings from plants.

The term seed treatment comprises all suitable seed treatment techniques known in the art, such as seed dressing, seed coating, seed dusting, seed soaking and seed pelleting.

Thus, the application of the formulation according to the present invention is carried out by spraying or dusting or otherwise applying the formulation according to the present invention to the seeds or the seedlings.

The present invention also comprises seeds coated with formulation according to the present invention.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the formulation according to the invention may also be used for the treatment seeds from plants, which tolerate the action of herbicides or fungicides or insecticides owing to breeding, including genetic engineering methods, for example seeds of transgenic crops which are resistant to herbicides from the group consisting of the sulfonylureas (EP-A-0257993, U.S. Pat. No. 5,013,659), imidazolinones (see for example U.S. Pat. No. 6,222,100, WO0182685, WO0026390, WO9741218, WO9802526, WO9802527, WO 04/106529, WO 05/20673, WO 03/14357, WO 03/13225, WO 03/14356, WO 04/16073), glufosinate-type (see for example EP-A-0242236, EP-A-242246) or glyphosate-type (see for example WO 92/00377) or in seeds of plants resistant towards herbicides selected from the group of cyclohexadienone/Aryloxyphenoxypropionic acid herbicides (U.S. Pat. No. 5,162,602, U.S. Pat. No. 5,290,696, U.S. Pat. No. 5,498,544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222) or in seeds of transgenic crop plants, for example cotton, with the capability of producing *Bacillus thuringiensis* toxins (Bt toxins) which make the plants resistant to certain pests (EP-A-0142924, EP-A-0193259)

The seed treatment application of the formulation according to the invention is carried out by spraying or dusting the seeds before sowing of the plants and before emergence of the plants by methods known to the skilled artisan.

In the treatment of seeds the corresponding formulations are applied by treating the seeds with an effective amount of the formulation according to the present invention.

Herein, the application rates of pesticide are generally from 0.1 g to 10 kg per 100 kg of seed, preferably from 1 g to 5 kg per 100 kg of seed, in particular from 1 g to 2.5 kg per 100 kg of seed. For specific crops such as lettuce or onion, the rate can be higher.

For the purpose of the present invention, seed treatment and soil (or habitat of plant) treatment is preferred.

The invention is further illustrated but not limited by the following examples.

EXAMPLES

To prepare the polymers, the following apparatus was used:

2 l open apparatus with process controlled water-bath, anchor stirrer and thermometer. The apparatus had connectors for 3 feeds, a reflux condenser and an inlet tube for introducting nitrogen or steam. Alternatively a 6 l closed apparatus without reflux condenser was used. This apparatus was used to synthesize polymers at temperatures higher than the boiling point of the solvent.

| Abbreviations used: | |
|---|---|
| VP | vinyl pyrrolidone |
| 4-Vpyr | 4-vinyl pyrridin |
| V59 | 2,2'-azobis(2-methylbutyronitrile) |
| IT | internal temperature |
| t | feed introduction time |
| VI | vinyl imidazole |
| iP | isopropanole |
| tBHP | tert. butyl dydroperoxide |
| NaBS | sodium bisulphite |

Example 1

Preparation of Polymer A

Preparation of a VP/4-Vpyr (75/25 mol %) copolymer, apparatus with reflux condenser.

The initial charge (65 g feed 1.15 g feed 2.27 g ethanol) was gassed with nitrogen and heated to a reactor internal temperature of 80° C. Then feed 1 (166.65 g VP, 52.7 g 4-Vpyr, 215 g ethanol) and 2 (2.19 g V59, 100 g ethanol) were started. Feed 1 was introduced in 4 h, feed 2 was introduced in the course of 5 h. The reaction mixture was then kept at 80° C. for additional 2 h. Then feed 3 (4.39 g V59, 50 g ethanol) was introduced in the course of 30 min. Again the reaction mixture was kept at 80° C. for additional 2 h. If the polymer was subject to quaternization the reaction mixture was diluted with 200 g of ethanol. If the polymer was used in its unquaternized form the ethanol was distilled of and the reaction mixture was subject to steam distillation.

Example 2

Preparation of Polymers B to F Apparatus with Reflux Condenser

Polymer B was prepared by quaternization of polymer A.

The initial charge (200 g of polymer A) was gassed with nitrogen and heated to a reactor internal temperature of 30° C. Then feed 1 (21.7 d diethyl sulfate) was introduced in the course of 1 h. After introduction of feed 1 the reaction vessel was kept for another hour at 30° C. and was then heated until reflux of the solvent. It was kept under reflux for additional 2 h. The ethanol was distilled of and the reaction mixture was subject to steam distillation. Following distillation, the polymer solution was diluted with 200 g water.

Polymerisation of the polymers C—F was carried out analogously to example 1. If a polymer was quaternized the quaternization was carried out analogously to example 2. The amounts and substances used for initial charge, feed 1, 2 and 3 are set forth in table 1.

Example 3

Root Uptake

To test the root systemicity of the polymers according to the present invention, radioactivly marked boscalid (prepared in analogy to EP 0545099 based on $^{14}$C marked pyridin) was used. For the tests wheat plants in vermiculite were drenched with boscalid/polymer solutions in water/acetone mixtures. As reference boscalid solutions in water/acetone mixtures without polymers were used [25 μl cold active solution (10000 ppm stock solution in acetone), 20 μl hot active solution (0.1 ppm in acetone, 1 μl corresponds to ~22000 Bcq), 25 μl acetone and 25 μl polymer solution (10000 ppm stock solution in water) were mixed and refilled with water to 10 ml]. After 48 and 120 hours leafs were cut from the plant and dissolved in Soluene 350 (60-80% toluene, 20-40% dodecyl (dimethyl)(tetradecyl)ammonium hydroxide, 2.5-10% methanol). Afterwards the radioactivity in the plant material was measured. High radioactivity in the plant material corresponds to high active ingredient uptake. Results are presented in table 2.

TABLE 2

|  | Time to measurement [h] | Uptake [Bcq] |
|---|---|---|
| Reference without polymer | 120 | 228 |
| Polymer A | 120 | 735 |
| Polymer B | 120 | 393 |
| Polymer C | 120 | 413 |
| Polymer D | 120 | 520 |

The results show that with polymers A-D, significantly improved root uptake was achieved.

Example 4

Leaf Uptake

To test the leaf uptake with polymers water/DMF solutions with radioactivly marked bentazone (prepared in analogy to

TABLE 1

|  |  | Initial charge | Feed 1 t = 4 h | Feed 2 t = 9 h | Feed 3 |
|---|---|---|---|---|---|
| Polymer C IT = 120° C. | Polymerisation Closed apparatus | 180 g ethanol 252 g feed 1 60 g feed 2 | 444.4 g VP 421.6 g 4-Vpyr 860 g ethanol | 33.2 g V59 450 g ethanol |  |
| Polymer D IT = 120° C. | Polymerisation Closed apparatus | 180 g ethanol 252 g feed 1 60 g feed 2 | 222.2 g VP 632.4 g 4-Vpyr 860 g ethanol | 33.2 g V59 450 g ethano |  |

|  |  | Initial charge | Feed 1 t = 3 h | Feed 2 batch | Feed 3 t = 30 min. |
|---|---|---|---|---|---|
| Polymer E IT = 85° C. | Polymerisation open apparatus | 50 g VI 450 g VP 1200 g water | 5 g V59 100 g iP | 3.6 g tBHP | 2.5 g NaBS 100 g Water |

|  |  | Initial charge | Feed 1 t = 1 h | Feed 2 | Feed 3 |
|---|---|---|---|---|---|
| Polymer F | Quaternization Open apparatus | 100 g polymer E 400 g ethanol | 26.4 g dodecyl bromide |  |  | methods known in the art, based on $^{14}C$ marked benzene) (1 µl cold active solution (10000 ppm solution in DMF), 10 µl hot active solution (0.1 ppm in DMF, ~2000000 counts/µl), 9 µl polymer solution (1000 ppm solution in water) and 80 µl DMF) were applied dropwise to the leaves of a wheat plants (10 drops per leaf). After 48 and 168 hours respectively. The leaves were cut off after the respective time and the excess active on the leaf surface eliminated by stripping the leaf with a cellulose acetate film. The leaves were then dissolved with Soluene 350 to determine the absolute amount of active ingredient that was taken up into the plant. As reference the active was applied in water/DMF solution without polymer. Results are presented in table 3.

TABLE 3

|  | Time to measurement [h] | Uptake [% of applied] |
|---|---|---|
| Reference without polymer | 48 | 5.7 |
|  | 168 | 8 |
| Polymer B | 48 | 26 |
|  | 168 | 23 |
| Polymer E | 48 | 13 |
|  | 168 | 33 |
| Polymer F | 48 | 30 |
|  | 168 | 36 |

The results show that with the polymers B, E and F significantly improved leaf uptake was achieved.

Example 5

Root Uptake

To test the root systemicity of fipronil with polymers, wheat plants in vermiculite were drenched with 20 ml fipronil/polymer (1:1 wt) solutions in hoagland solution/acetone mixtures (0.6 v % acetone). Two fipronil and polymer concentrations were used, 3 ppm and 6 ppm. As reference fipronil solutions in Hoagland solution/acetone mixtures without polymer were used. Hoagland solution consists of the following ingredients: 0.25 v % of 1M KNOB solution in water, 0.1 v % of 1M $MgSO_4$ solution in water, 0.05 v % of 1M $KH_2PO_4$ solution in water, 0.25 v % 1M $Ca(NO_3)_2$) solution in water, 0.05 v % of a trace solution consisting of 2.86 g/l $H_3BO_3$, 1.81 g/l $MnCl_2*4H_2O$, 0.22 g/l $ZnSO_4*7H_2O$, 0.08 g/l $CuSO_4*5H_2O$, 0.016 g/l $MoO_3$ in water, 0.075 v % Sequestrene 138 Fe consisting of 30 g/l sodium ferric ethylenediamine di-(o-hydroxyphenylacetate) in water, 99.225 v % water sterilized and pH adjusted to 6-6.5 with NaOH.

The plants where then infested with aphids. After 4 days the aphid population on the wheat plants was counted. The results of fipronil and fipronil with polymer are related to the aphid population on plants that had not been treated with fipronil. Results are presented in table 4.

TABLE 4

|  | Concentration [ppm] | Aphid population |
|---|---|---|
| Not treated | 0 | 100% |
| Reference without polymer | 3 | 38% |
|  | 6 | 23% |
| Polymer A | 3 | 7% |
|  | 6 | 2% |
| Polymer C | 3 | 3% |
|  | 6 | 1% |

The results show that with the polymers A and C significant improved pest control was achieved for both concentrations.

Example 6

Seed Treatment

To test the polymers, 100 µL COSMOS® 50 FS (a commercially available aqueous suspension concentrate for seed treatment from BASF Aktiengesellschaft comprising 500 g/L fipronil) was mixed with 1100 µL of a 4.5 wt % polymer solution in water. As a reference ("COSMOS® 50 FS without polymer") a mixture of 100 µL COSMOS® 50 FS in 1100 µL water was used. Then 100 sugar beet seeds were treated twice with 300 µl polymer/COSMOS® 50 FS mixture (corresponding to 25 g Fipronil/100 kg seed and 25 g polymer/100 kg seed), and another 100 seeds were treated twice with 300 µl of the reference ("COSMOS® 50 FS without polymer").

The seeds of sugar-beets were sown in soil containing styropor-boxes under greenhouse conditions. Samples were taken at a plant height of about 10-15 cm. After sampling the plants (both treatment groups) were subdivided into two segments (hypocotyl and rest of plant). The samples were frozen immediately after sampling and kept frozen until analysis. Prior to analyses the sample material was homogenized using a Stephansmill in the presence of dry ice resulting in very small sample particles. Fipronil was extracted from plant matrices using a mixture of methanol and water. For clean-up a liquid/liquid partition against dichloromethane was used. The final determination of fipronil content was performed by HPLC-MS/MS. Results are presented in table 4.

TABLE 4

|  |  | Fipronil concentration [ppm] |
|---|---|---|
| COSMOS ® 50 FS without polymer | Hypocotyl | 0.1836 |
|  | Rest of plant | 0.0624 |
| COSMOS ® 50 FS with polymer C | Hypocotyl | 1.5828 |
|  | Rest of plant | 0.081 |

The results show that with the polymer C, significant improved root uptake was achieved in seed treatment experiments.

The invention claimed is:
1. A formulation comprising
at least one pesticide and
at least one co-polymer comprising
a) a N-vinylamid comonomer a) of formula I

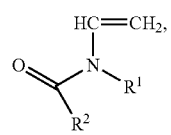

(I)

wherein $R^1$ and $R^2$ are independently of one another hydrogen or $C_1$-$C_4$ alkyl, or $R^1$ and $R^2$ together form a —$(CH_2)_x$— moiety, which forms together with the nitrogen and the carbonyl-moiety a 5-8 membered ring; and
b) at least one comonomer b) selected from the group consisting of vinylpyrridin, vinylpyrridin derivatives and N-vinylimidazole in polymerized form.

2. The formulation of claim 1, wherein said copolymer comprises 90-10 wt % of comonomer a); and 10 to 90 wt % of comonomer b).

3. The formulation of claim 2, wherein the % by weight of the individual components of the copolymer add up to 100% by weight.

4. The formulation of claim 1, wherein said copolymer comprises 2-vinylpyridin, 3- vinylpyridin, 4- vinylpyridin or vinyl-2-methyl-5- pyridin as comonomer b).

5. The formulation of claim 1, wherein said copolymer comprises 1-vinyl-2-pyrrolidinone as comonomer a).

6. The formulation of claim 1, wherein said copolymer comprises 1-vinyl-2-pyrrolidinone as comonomer a); and 4 vinylpyrridin as comonomer b).

7. The formulation of claim 1, further comprising formulation auxiliaries.

8. The formulation of claim 1, wherein said pesticide is a pesticide which confers plant health effects.

9. A method of combating harmful insects and/or phytopathogenic fungi, which comprises contacting plants, seed, soil or habitat of plants in or on which the harmful insects and/or phytopathogenic fungi are growing or may grow, plants, seed or soil to be protected from attack or infestation by said harmful insects and/or phytopathogenic fungi with an effective amount of the agrochemical formulation of claim 1.

10. A method of controlling undesired vegetation, which comprises allowing a herbicidally effective amount of the agrochemical formulation of claim 1 to act on plants, their habitat or on seed of said plants.

11. A method of improving the health of plants, which comprises applying a formulation of claim 8, to plants, parts of plants, or the locus where plants grow.

12. Seeds comprising a formulation of claim 1.

13. The formulation of claim 1, wherein $R^1$ and $R^2$ are hydrogen.

14. A method of preparing a pesticide with increased systemicity comprising:
combining at least one pesticide and at least one copolymer comprising
a) a N-vinylamid comonomer a) of formula I

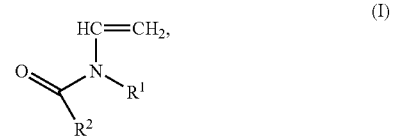

wherein $R^1$ and $R^2$ are independently of one another hydrogen or $C_1$-$C_4$ alkyl, or $R^1$ and $R^2$ together form a —$(CH_2)_x$ moiety, which forms together with the nitrogen and the carbonyl-moiety a 5-8 membered ring; and
b) at least one comonomer b) selected from the group consisting of vinylpyrridin, vinylpyrridin derivatives and N-vinylimidazole in polymerized form, wherein a pesticide with increased systemicity is prepared.

* * * * *